United States Patent
Cheong et al.

(10) Patent No.: US 8,313,744 B2
(45) Date of Patent: Nov. 20, 2012

(54) COMPOSITION FOR THE PREVENTION AND TREATMENT OF ABSENCE SEIZURES COMPRISING PKC AGONIST AS AN EFFECTIVE INGREDIENT

(75) Inventors: Eunji Cheong, Seoul (KR); Hee-Sup Shin, Gyeonggi-do (KR); Yihong Zheng, Seoul (KR); Kyoobin Lee, Seoul (KR); Jungryun Lee, Gyeonggi-do (KR); Seongwook Kim, Gyeonggi-do (KR); Maryam Sanati, Seoul (KR); Sukyung Lee, Seoul (KR); Yeon-Soo Kim, Seoul (KR); Sukchan Lee, Daejeon (KR)

(73) Assignee: Korea Institute of Science and Technology, Seoul (KR)

( * ) Notice: Subject to any disclaimer, the term of this patent is extended or adjusted under 35 U.S.C. 154(b) by 154 days.

(21) Appl. No.: 12/851,137

(22) Filed: Aug. 5, 2010

(65) Prior Publication Data

US 2011/0243917 A1 Oct. 6, 2011

(30) Foreign Application Priority Data

Apr. 2, 2010 (KR) ........................ 10-2010-0030612

(51) Int. Cl.
- *A61K 38/48* (2006.01)
- *A61K 31/21* (2006.01)
- *A61K 31/12* (2006.01)
- *A61K 31/045* (2006.01)
- *A61K 31/015* (2006.01)
- *A01N 37/00* (2006.01)
- *A01N 35/00* (2006.01)
- *A01N 31/00* (2006.01)
- *A01N 27/00* (2006.01)

(52) U.S. Cl. ..................... 424/94.64; 514/510; 514/691; 514/729; 514/739; 514/763

(58) Field of Classification Search ..................... None
See application file for complete search history.

(56) References Cited

FOREIGN PATENT DOCUMENTS

WO WO 2009/093772 7/2009

OTHER PUBLICATIONS

Smith et al. European Journal of Pharmacology, vol. 213, 1992, pp. 133-135.*
Cheong et al., "Tuning Thalamic Firing Modes via Simultaneous Modulation of T- and L-Type $Ca^{2+}$ Channels Controls Pain Sensory Gating in the Thalamus," *The Journal of Neuroscience*, vol. 28, No. 49, pp. 13331-13340, 2008.
Cheong et al., "Deletion of phospholipase C β4 in thalamocortical relay nucleus leads to absence seizures," *PNAS*, vol. 106, No. 51, pp. 21912-21917, 2009.
Kang et al., "Expression of Kir2.1 Channels in Astrocytes Under Pathophysiological Conditions," *Molecules and Cells*, vol. 25, No. 1, pp. 124-130, 2008.
Shin et al., "Phospholipase C β4 in the Medial Septum Controls Cholinergic Theta Oscillations and Anxiety Behaviors," *The Journal of Neuroscience*, vol. 29, No. 49, pp. 15375-15385, 2009.

* cited by examiner

*Primary Examiner* — Chris R Tate
*Assistant Examiner* — Douglas F White
(74) *Attorney, Agent, or Firm* — Ladas & Parry LLP

(57) ABSTRACT

The present invention relates to a composition comprising PKC agonist as an active ingredient. More precisely, the present inventors confirmed that absence seizure specific SWD was reduced by administrating PKC agonist into an animal model. Therefore, the composition of the present invention comprising PKC agonist as an active ingredient can be effectively used for the prevention and treatment of absence seizure and for the production of health improving functional food.

7 Claims, 6 Drawing Sheets

[Fig. 1]
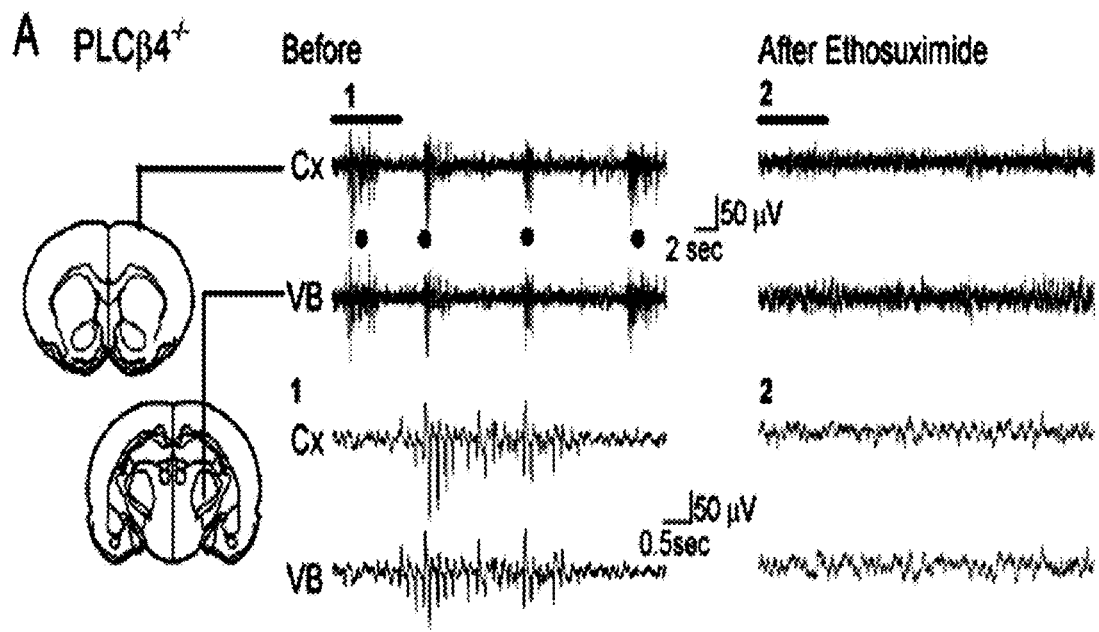
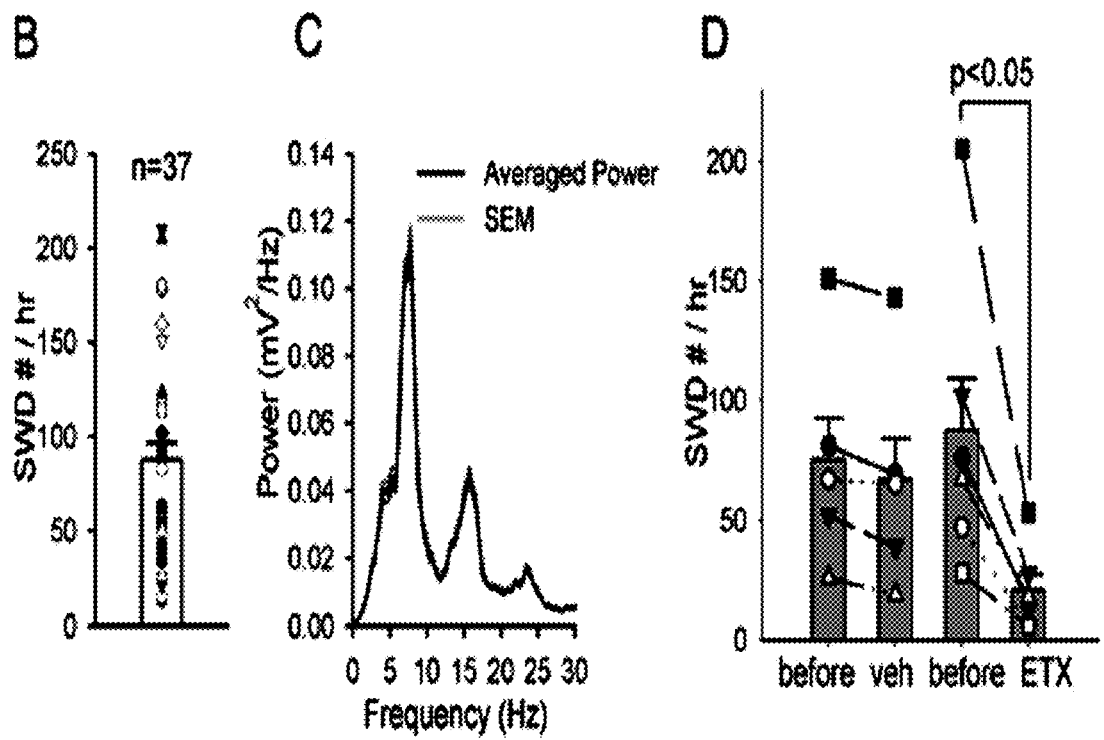

[Fig. 2]
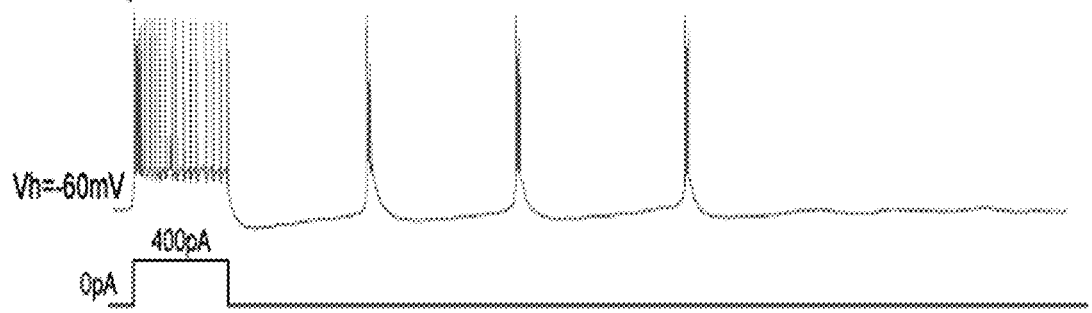
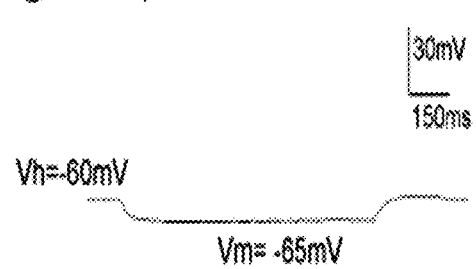
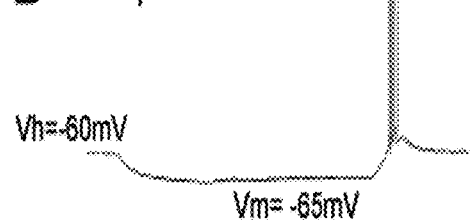
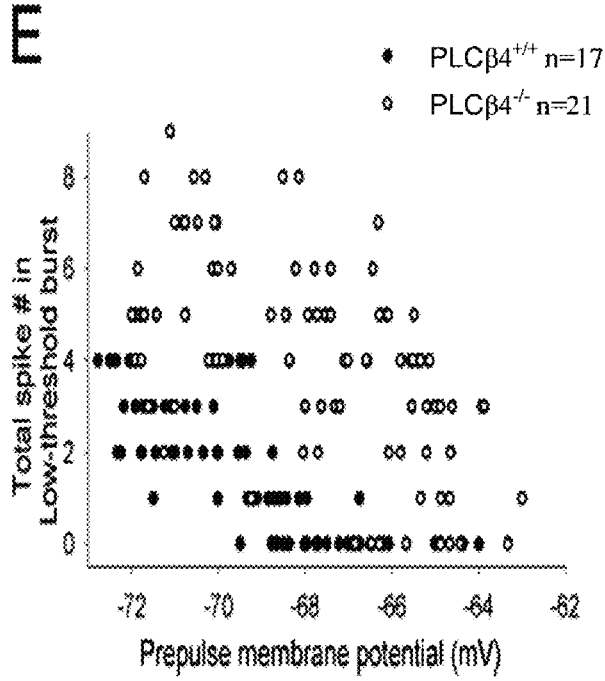

[Fig. 3]
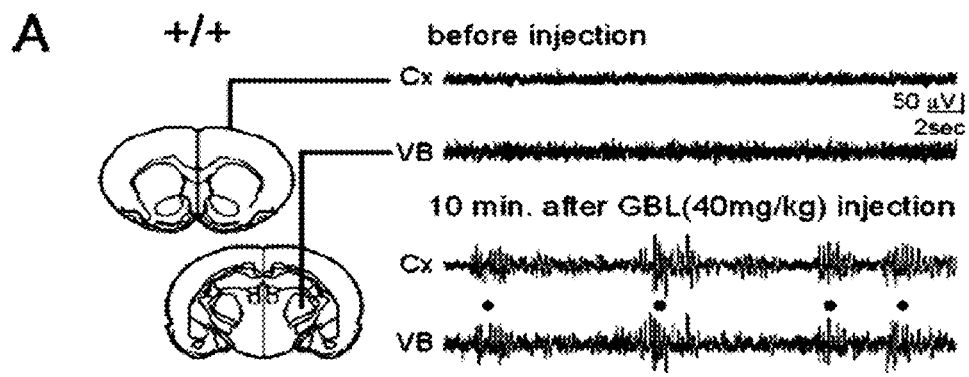
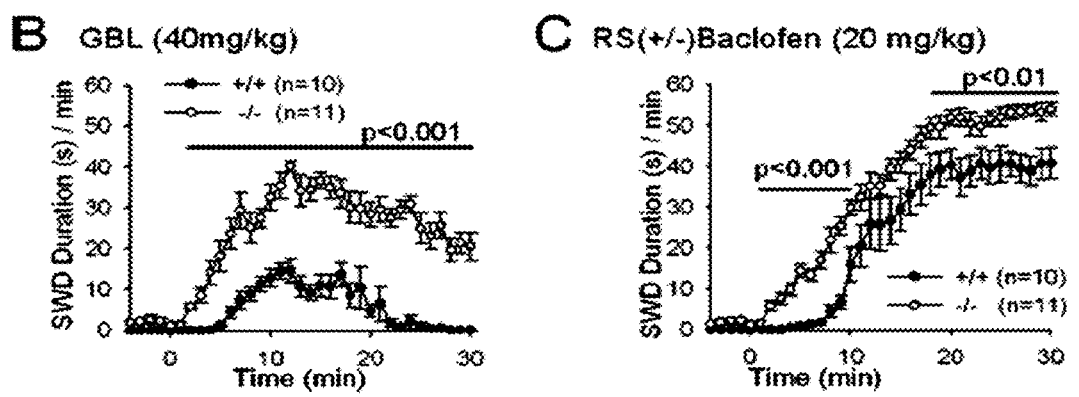
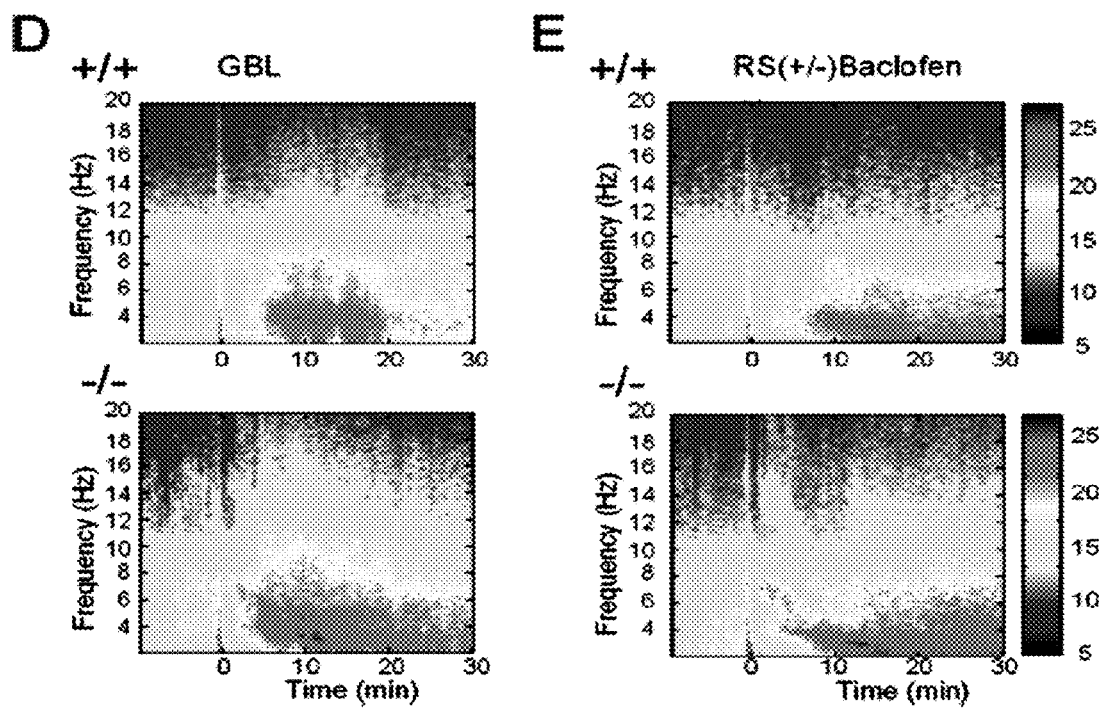

[Fig. 4]
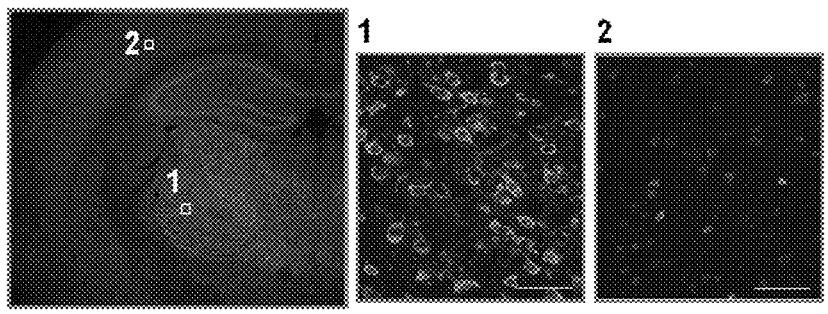
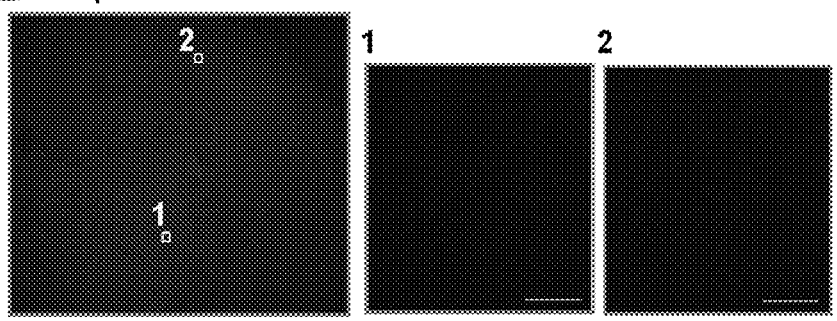
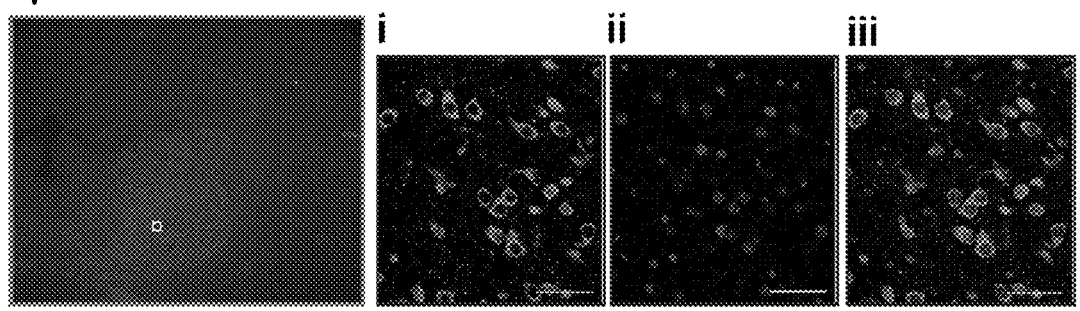
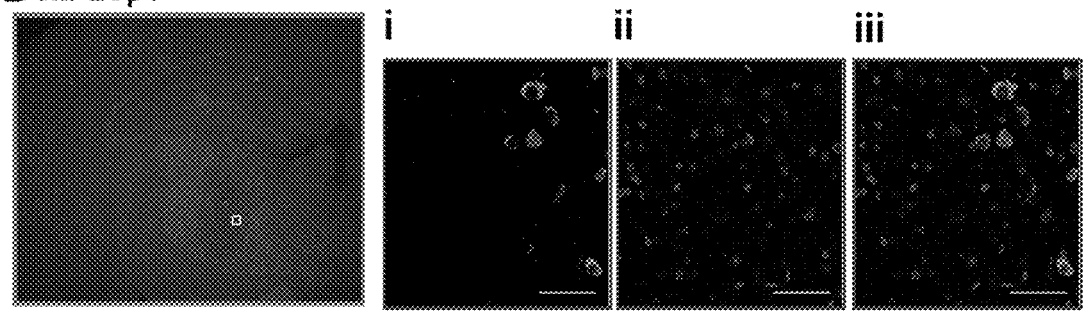

[Fig. 5]
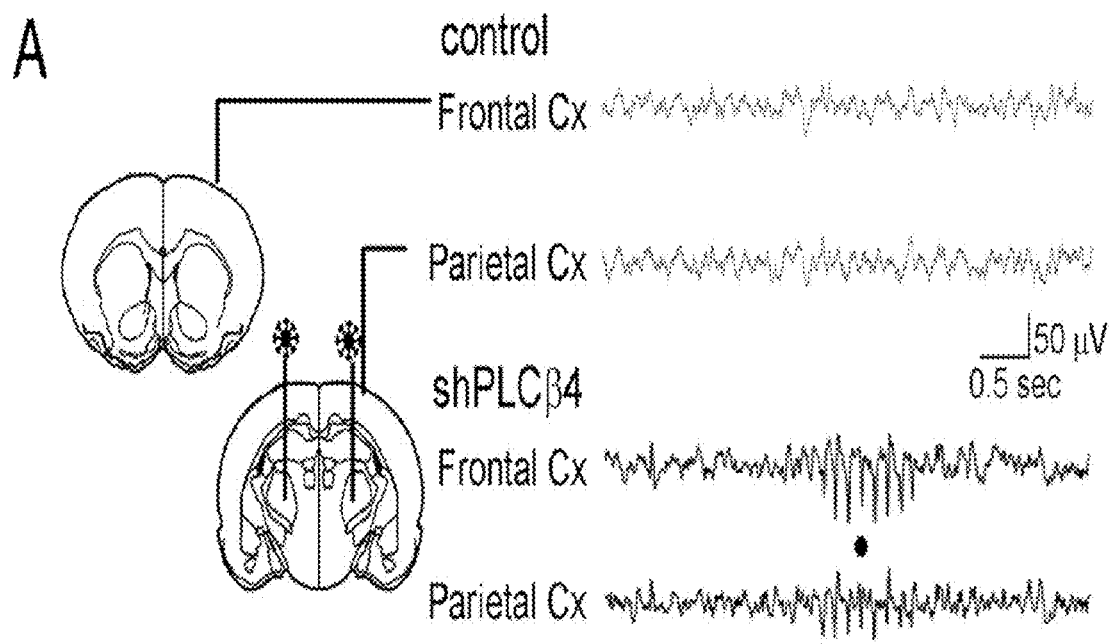
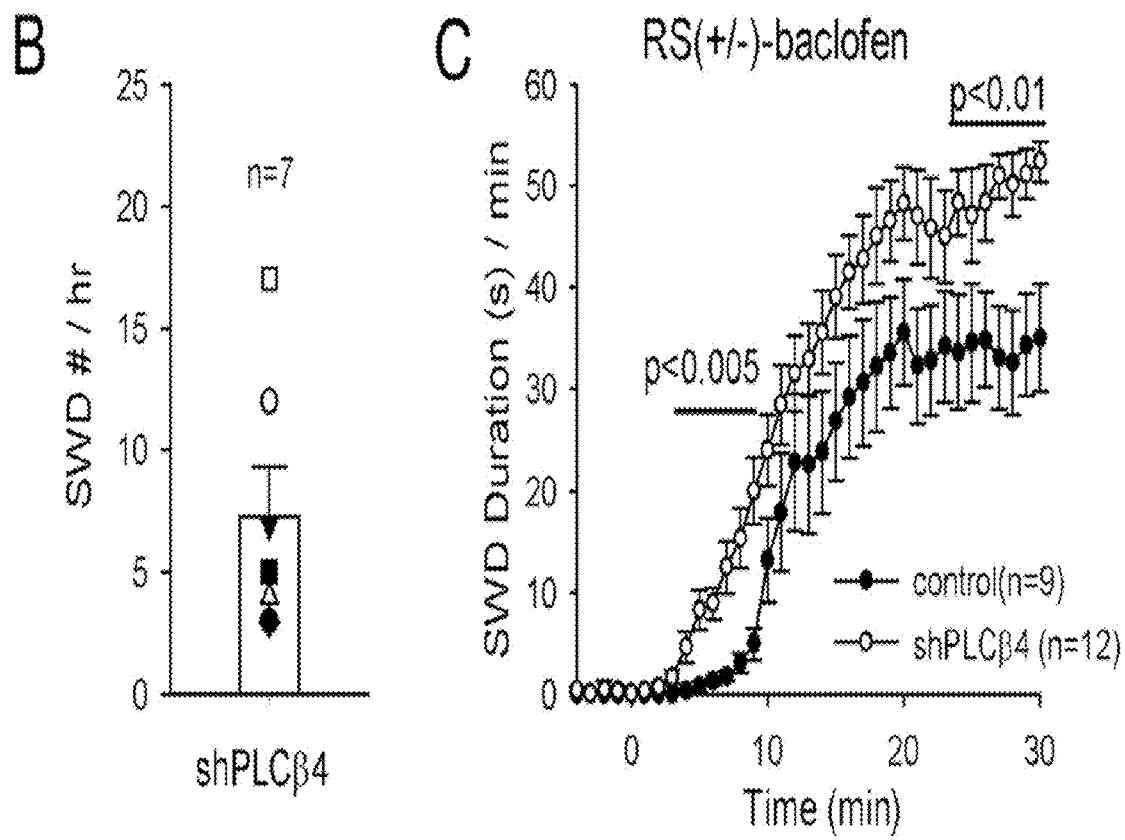

[Fig. 6]
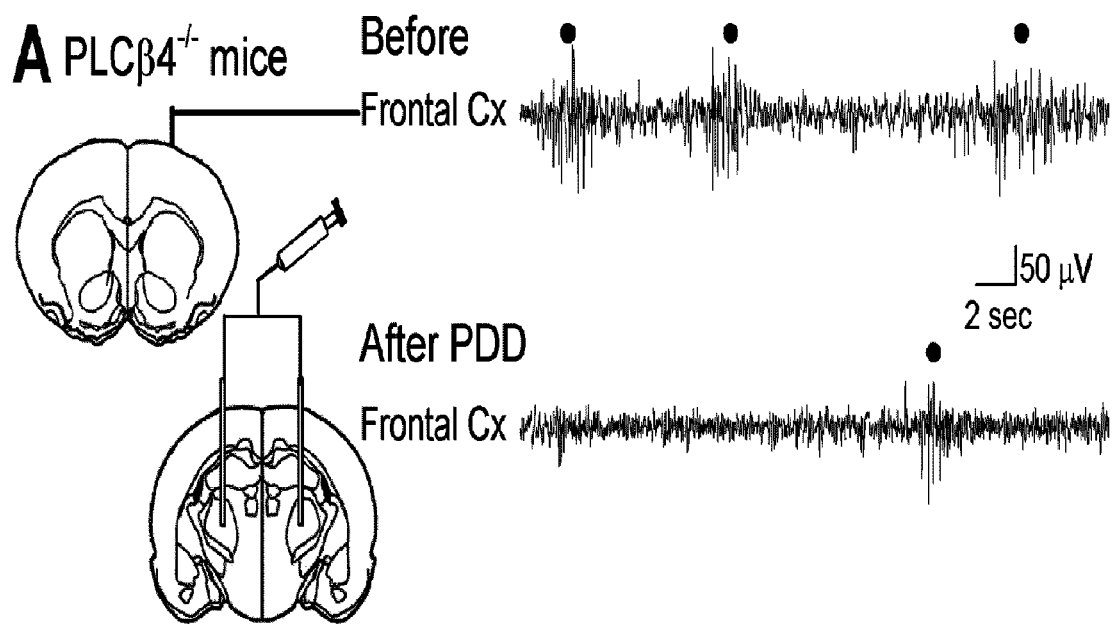
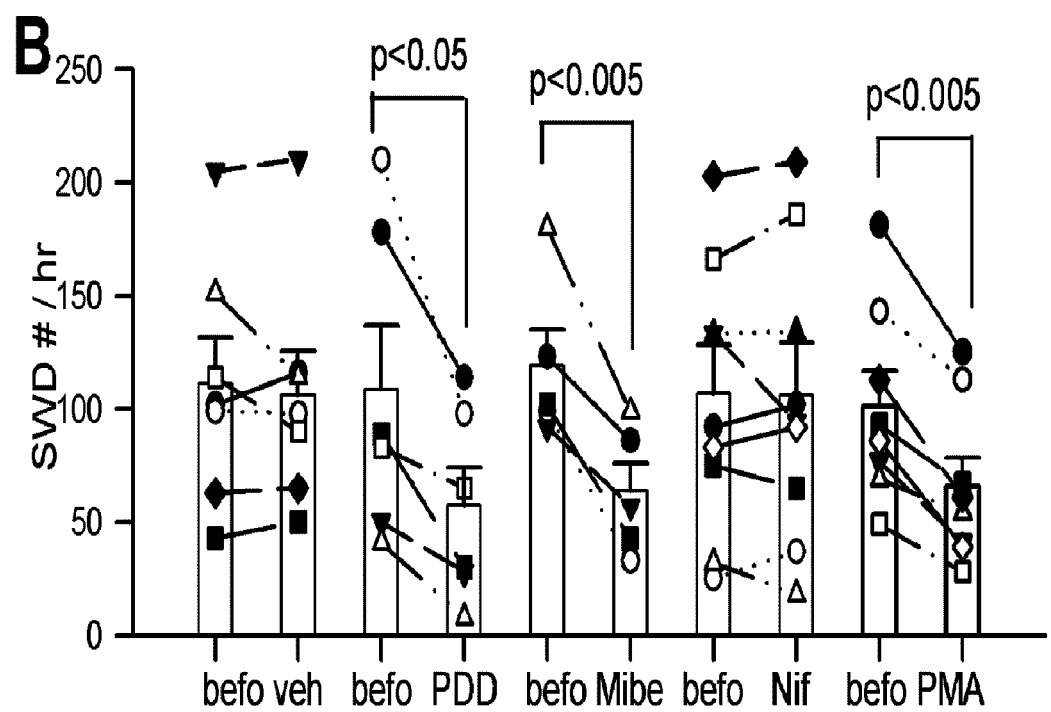

COMPOSITION FOR THE PREVENTION AND TREATMENT OF ABSENCE SEIZURES COMPRISING PKC AGONIST AS AN EFFECTIVE INGREDIENT

CROSS-REFERENCES TO RELATED APPLICATION

This patent application claims the benefit of priority from Korean Patent Application No. 10-2010-0030612, filed on Apr. 2, 2010, the contents of which are incorporated herein by reference.

BACKGROUND OF THE INVENTION

1. Field of the Invention

The present invention relates to a composition for the prevention and treatment of absence seizure comprising PKC agonist as an active ingredient.

2. Description of the Related Art

Epilepsy is a seizure disease whose beginning symptom is loss of consciousness with tonic convulsion cramp followed by clonic convulsion. The cause of this disease is presumably mesial temporal sclerosis, brain tumor, trauma, stroke, congenital disorder, and brain infection, which is believed not inherited.

Epilepsy is largely divided into two categories, which are generalized seizure and partial seizure. Generalized seizure is characterized by the simultaneous overall seizure in the total area of cerebrum. Clinically, generalized seizure begins simultaneously in the right and the left side of the body which accompanies loss of consciousness. So, when electroencephalography is performed, epilepti form discharge is observed overall in both sides of cerebrum. Generalized seizure includes the following sub-types: tonic clonic seizure, petit mal seizure, myoclonic seizure, and atonic seizure. Tonic clonic seizure is also called as grand mal seizure and is the most frequent type of seizure. When tonic clonic seizure begins, a subject loses his consciousness abruptly without any warning sign, followed by convulsions in muscles over the whole body. Seizure progresses from the early tonic phase, which is the stage of body stiffness, to the late clonic phase, that is the stage of shaking body. Petit mal seizure is mainly observed among children at the age group of 5-7 years old, which allegedly disappears after puberty. It accompanies unconsciousness for several seconds, blinking, and light muscle cramp. Myoclonic seizure is the temporary acute muscular contraction in the whole body without losing consciousness as if a sudden shock. Atonic seizure is characterized by sudden body weakness with shock, unlike spasm.

Partial seizure shows warning signs when it beings. Partial seizure is divided into complex partial seizure and simple partial seizure according to the clouding of consciousness. However, in the early stage of partial seizure, epilepti form discharge is apt to be dispersed to both sides of the brain, so that it progresses into generalized seizure. Complex partial seizure takes ⅔ of the total seizures, whose symptoms vary with patients. The light complex partial seizure looks like petit mal seizure, while the severe complex partial seizure shows similar symptoms to grand mal seizure. So, it is most difficult to be diagnosed. After the warning signs such as auditory hallucination, olfactory hallucination and visual hallucination, automatism which is characterized by repeated hands, feet, and mouth movement, and other behavioral symptoms such as turning the body one side or yelling, or leaning power on one arm and one leg can be observed, but the patient cannot recognize his own symptoms. Simple partial seizure happens locally in a part of the brain particularly in the part responsible for a specific function. It is generally known that such simple partial seizure occurs in the motor cortex or sensory cortex of the brain.

Absence seizure is a kind of epilepsy that does not carry seizure. It only shows unconsciousness for a moment and SWD (spike-and-wave discharge). In thalamocortical (TC) neurons, low voltage dependent burst firing is accompanied. This seizure shows two different sub-types: one is observed in infancy at the age of around 6 and the other is observed in adolescence at the age of around 12. The frequency of this seizure is higher in women. It can be triggered by hyperventilation and photic stimulation. Absence seizure takes 10% of total seizures outbreaking in children. However, the mechanism of absence seizure is still not disclosed. Accordingly, the treatment method has not been established.

The object of the treatment for absence seizure is to reduce frequency of seizure eventually to prevent injury during unconsciousness including seizure or to improve memory loss or other troubles in daily life resulted from the seizure and to reduce side effects that could be more serious than the seizure itself.

For the treatment of epilepsy, drugs for oral administration such as Phenytoin, Carbamazepine, Valproic acid, Phenobarbital, ethosuximide, Clonazepam, clobazam and Primidone have been used. Recently, the treatment of epilepsy becomes more advanced owing to the newly developed drugs like vigabatrin, Zonisamide, Lamotrigine, topiramate, Oxcarbazepine and Gabapentine, etc. However, the results of the treatment of epilepsy using the said medicines are not satisfactory. The chances of controlling epilepsy with a single medicine are 60-70% and 20-25% requires co-administration of different medicines. The last 10% does not show any improvement with any of the said medicines.

Make matter worse, the said drugs carry side effects. For example, Clonazepam can bring the medicinal effect shortly after the administration but resistance to this drug and other side effects are observed frequently. It was also reported that Clonazepam could cause damage in the liver. So, Clonazepam is not recommended. Even though the said drugs are effective in the treatment of absence seizure, the known side effects are serious and prescription has to be different over the cause of the seizure. Thus, the administration of those drugs has to be done after doctor's diagnosis.

Therefore, the present inventors tried to develop a novel therapeutic agent for absence seizure, and finally completed this invention by confirming that SWD, the characteristic of absence seizure, was reduced when PKC agonist was administered to the phospholipase C beta4 (PLCβ4) knock-out mouse.

SUMMARY OF THE INVENTION

It is an object of the present invention to provide a composition for the prevention and treatment of absence seizure comprising PKC agonist as an active ingredient, a method for the treatment of absence seizure, a method for screening PKC agonist, and health food for the improvement of absence seizure.

To achieve the above object, the present invention provides a composition for the prevention and treatment of absence seizure comprising PKC agonist as an active ingredient.

The present invention also provides a method for the treatment of absence seizure comprising the step of administering PKC agonist to a subject with absence seizure.

The present invention further provides a method for the prevention of absence seizure comprising the step of administering PKC agonist to a subject.

The present invention also provides a screening method of PKC agonist for the prevention and treatment of absence seizure comprising the following steps:

1) contacting a sample compound with PKC in vitro;
2) selecting a compound that increased PKC activity, compared with the control untreated with the sample compound of the step 1); and
3) determining whether or not the selected sample compound could be a candidate for the preventive and therapeutic agent for absence seizure.

In addition, the present invention provides a screening method of PKC agonist for the prevention and treatment of absence seizure comprising the following steps:

1) contacting a sample compound with PKC expressing cells in vitro;
2) selecting a compound that increased PKC activity, compared with the control untreated with the sample compound of the step 1); and
3) determining whether or not the selected sample compound could be a candidate for the preventive and therapeutic agent for absence seizure.

Advantageous Effect

When PKC agonist was administered to the PLCβ4 knock-out mouse, the model for the confirmation of the effect of the therapeutic agent for absence seizure of the present invention, the absence seizure specific SWD was reduced. Therefore, the PKC agonist of the present invention can be effectively used for the preparation of the composition for the prevention and treatment of absence seizure, for the development of a treatment method of absence seizure and a screening method of PKC agonist, and for the production of health improving functional food.

BRIEF DESCRIPTION OF THE DRAWINGS

The application of the preferred embodiments of the present invention is best understood with reference to the accompanying drawings, wherein:

FIG. 1 is a set of diagrams illustrating spontaneous absence seizure developed in the PLCβ4 knock-out mouse:

FIG. 1A is a diagram illustrating the observation of electroencephalogram (EEG) on the frontal cortex and on the ventrobasal complex before and after the administration of ethosuximide to the PLCβ4 knock-out mouse;
  Cx: frontal cortex;
  VB: ventrobasal complex;

FIG. 1B is a graph illustrating the frequency of SWD observed in the PLCβ4 knock-out mouse;

FIG. 1C is a graph illustrating the result of power spectrum of spontaneous SWD;
  Averaged Power: mean value of frequency power spectrum of each animal;
  SEM: standard error of mean value;

FIG. 1D is a graph illustrating the observation of SWD before and after the administration of ethosuximide;
  before: before the administration;
  veh: control group treated with NaCl; and
  ETX: experimental group treated with ethosuximide.

FIG. 2 is a set of diagrams illustrating the multiple sclerosis increased in thalamocortical neurons in the PLCβ4 knock-out mouse:

FIG. 2A is a diagram illustrating that burst firing was not observed in thalamocortical neurons of a normal mouse after inducing single firing by applying depolarization current;

FIG. 2B is a diagram illustrating the conversion of neurons into burst firing mode after inducing single firing by applying depolarization current in thalamocortical neurons in the PLCβ4 knock-out mouse;

FIG. 2C is a diagram illustrating that burst firing was not observed when the cell membrane of the normal mouse thalamocortical neuron was applied with prepulse at the level of −65 mV, which was significant enough to cause hyperpolarization;

FIG. 2D is a diagram illustrating the burst firing observed in thalamocortical neurons of the PLCβ4 knock-out mouse after applying prepulse on the cell membrane at the level of −65 mV, which was significant enough to cause hyperpolarization; and FIG. 2E is a diagram illustrating the number of burst firing spike observed in a normal mouse and in the PLCβ4 knock-out mouse when −73~−63 mV of pulse was applied.

FIG. 3 is a set of diagrams illustrating that SWD was reduced after the administration of a drug for absence seizure to the PLCβ4 knock-out mouse:

FIG. 3A is a diagram illustrating the observation of electroencephalogram (EEG) on the frontal cortex and on the ventrobasal complex before and after the administration of γ-butyrolactone to the PLCβ4 knock-out mouse and a normal mouse;
  Cx: frontal cortex;
  VB: ventrobasal complex;
  GBL: γ-butyrolactone;

FIG. 3B is a diagram illustrating SWD observed in the PLCβ4 knock-out mouse and a normal mouse after the administration of γ-butyrolactone;

FIG. 3C is a diagram illustrating SWD observed in the PLCβ4 knock-out mouse and a normal mouse after the administration of RS(+/−)-baclofen;

FIG. 3D is a diagram illustrating the power spectrums observed in the PLCβ4 knock-out mouse and a normal mouse after the administration of γ-butyrolactone; and FIG. 3E is a diagram illustrating the power spectrums observed in the PLCβ4 knock-out mouse and a normal mouse after the administration of RS(+/−)-baclofen.

FIG. 4 is a set of diagrams illustrating the local decrease of PLCβ4 protein expression particularly into the thalamus after the microinjection of LV-shPLCβ4 vector in the thalamus:

FIG. 4A is a diagram illustrating the expression of PLCβ4 protein in the thalamus and the frontal lobe of a normal mouse;

FIG. 4B is a diagram illustrating the expression of PLCβ4 protein in the thalamus and the frontal lobe of the PLCβ4 knock-out mouse;

FIG. 4C is a diagram illustrating the expression of PLCβ4 protein in the thalamus and the frontal lobe of the PLCβ4 knock-out mouse after the microinjection of pLKO vector into the thalamus;
  pLKO-control: non-specific control vector;

FIG. 4D is a diagram illustrating the expression of PLCβ4 protein in the thalamus and the frontal lobe of a normal mouse after the microinjection of LV-shPLCβ4 vector into the thalamus; and
  shPLCβ4: lentivirus vector containing PLCβ4 short hairpin RNA.

FIG. 5 is a set of diagrams illustrating absence seizure observed limitedly in the thalamic nucleus of the PLCβ4 knock-out mouse:

FIG. 5A is a diagram illustrating EEG observed after the microinjection of pLKO vector and LV-shPLCβ4 vector limitedly in the thalamus;

Frontal Cx: frontal lobe;

Pariel Cx: pariel lobe;

FIG. 5B is a diagram illustrating the number of SWD observed after the microinjection of LV-shPLCβ4 vector;

FIG. 5C is a diagram illustrating the comparison of SWD duration generated by the administration of RS(+/−)-baclofen after the microinjection of pLKO vector and LV-shPLCβ4 vector limitedly in the thalamus; and control: pLKO vector microinjected group.

FIG. 6 is a set of diagrams illustrating the decrease of SWD after the microinjection of PKC agonist and calcium channel inhibitor limitedly in the thalamus of the PLCβ4 knock-out mouse:

FIG. 6A is a diagram illustrating EEG before and after the injection of PDD in the PLCβ4 knock-out mouse;

PDD: phorbol 12,13-didecanoate;

FIG. 6B is a diagram illustrating the comparison of SWD number before and after the administration of PDD, PMA, mibefradil, and nifedipine;

before: before the administration;

Mibe: mibefradil;

Nif: nifedipine; and

PMA: Phorbol 12-Myristate 13-Acetate (PMA).

DESCRIPTION OF THE PREFERRED EMBODIMENTS

The terms used in this invention are described hereinafter.

Electroencephalogram (EEG) indicates the plot in which brain wave is recorded. The brain cells cause a regular electric shock which shows a unique pattern. This is called "brain wave". Absence seizure is a kind of epilepsy that is not accompanied by seizure. The symptom of absence seizure is a temporary unconsciousness. When EEG is measured under absence seizure, SWD (spike-and wave discharge) is characteristically observed. Reports have been made on the electrophysiological relevance of epilepsy mostly showing spike-and wave. Particularly, according to the intracellular recording, there has always been "spike" pattern in brain wave involved in neuronal firing. In the meantime, "wave" pattern in brain wave has been confirmed to be involved in hyperpolarized neurons (Pollen D A, Clin. Neurophysiol. 17, 398-404 1964). The "spike" of EEG is related to "firing" and the "wave" is related to "silence".

PLCβ4 (phospholipase C beta 4) is a kind of phospholipase C (PLC). A change of the firing mode is observed in brain wave of the thalamus of the PLCβ4 knock-out mouse, and this change is allegedly resulted from behavioral factors with carrying pain response (Cheong et al, 2008, The Journal of Neuroscience). This report is valuable among many researches reporting changes in firing mode of the thalamus because it has recorded the connection between the firing mode change with the direct behavioral acts. Moreover, the report disclosed that pain could be reduced by inhibiting the activity of protein kinase C, the downstream molecule of PLCβ4, indicating that PLCβ4-PKC signal transduction plays a role as "molecular switch" that blocks pain reception. There are a few other patent documents about a use of the PLCβ4 knock-out mouse as an anxiety disorder animal model (Korean Patent Publication No. 10-2009-0081232) and a method of treating anxiety disorder by inhibiting T-type calcium channel of the PLCβ4 knock-out mouse (Korean Patent No. 10-0958291). However, there is no prior art in relation to absence seizure in the PLCβ4 knock-out mouse.

Protein kinase C (PKC) is a kind of enzymes related to the regulation of the protein functions via phosphorylation of serine and threonine residues. Protein kinase C is activated by the increase of diacylglycerol or $Ca^{2+}$ concentration and plays an important role in diverse intracellular signal transduction pathways. Protein kinase C is a downstream molecule of PLCβ4 that is known to inhibit the activation of T-type $Ca^{2+}$ channel.

Hereinafter, the present invention is described in detail.

The present invention provides a method for treating absence seizure comprising the step of administering a pharmaceutically effective dose of PKC agonist to a subject with absence seizure.

The said PKC agonist is preferably phorbol 12,13-didecanoate (PDD), phorbol 12-Myristate 13-Acetate (PMA), 12-O-tetradecanoyl-phorbol-13-acetate (TPA), bryostatin 1, thrombin, thromboxane mimetic, 1-hexylindolactam-V10, cholesterol sulfate, daphnoretin, decursin, dicaprylglyceride (DiC8), farnesyl thiotriazole, mezerein, 3-ingenyl angelate (PEP005), or sapintoxin A, but not always limited thereto.

In the method of treating absence seizure of the present invention, the effective dose of PKC agonist is preferably 1~20 pmole, more preferably 5~15 pmole, and most preferably 10 pmole, but not always limited thereto. The symptoms of absence seizure herein are one or more symptoms selected from the group consisting of seizure, tension-free symptom, fainting and spike-and-wave discharges (SWD), but not always limited thereto. And the SWD is preferably measured by recording EEG. In the method of treating absence seizure herein, the PKC agonist is preferably administered by parenteral administration pathway, which is preferably intracerebral administration and more preferably intrathalamic administration, but not always limited thereto.

The subject herein is preferably a mammal, which is exemplified by human, non-human primate, mouse, rat, dog, cat, rabbit, horse, and cow, but not always limited thereto.

In a preferred embodiment of the present invention, the inventors observed brain wave of the PLCβ4 knock-out mouse after the administration of ethosuximide, one of absence seizure therapeutic agents, in order to disclose the relevance of absence seizure and the PLCβ4 knock-out mouse. Before the administration of ethosuximide, spike-and-wave discharge, the characteristic brain wave of absence seizure, was observed in the frontal lobe and the ventrobasal complex. After the administration of ethosuximide, the SWD was reduced (see FIG. 1). From the result, it was confirmed that the PLCβ4 knock-out mouse can be used as an epilepsy animal model.

In another preferred embodiment of the present invention, the effect of the firing pattern of the PLCβ4 knock-out mouse on SWD, one of the characteristics of absence seizure, was investigated. To do so, diverse depolarization currents were applied on the brain slices obtained from both a normal mouse and the PLCβ4 knock-out mouse, followed by observation of firing patterns in thalamocortical neurons. As a result, tonic firing was observed at first both in the normal mouse and in the PLCβ4 knock-out mouse after the application of depolarization current. Then, burst firing was observed only in the PLCβ4 knock-out mouse. That is, the change of mode from tonic firing to burst firing was observed in the PLCβ4 knock-out mouse but not in the normal mouse. When −73~−63 my depolarization current was applied into a normal and the PLCβ4 knock-out mouse, the change of mode into burst firing was also observed only in the PLCβ4 knock-out mouse even with the application of a lower depolarization current (see FIG. 2).

In a preferred embodiment of the present invention, the $GABA_B$ receptor agonist γ-butyrolactone (GBL) (type B γ-aminobutyric acid receptor agonist) known as a drug inducing absence seizure, or the specific $GABA_B$ receptor agonist RS(+/−)-baclofen was injected in the PLCβ4 knock-out mouse. Then, sensitivity of the PLCβ4 knock-out mouse to absence seizure was measured. After administering the said GABA$_B$ receptor agonist into the normal mouse and the PLCβ4 knock-out mouse, brain wave was observed in the frontal lobe and the ventro-basal complex. As a result, SWD was retained longer than in the normal mouse not treated with the GABA$_B$ receptor agonist. The consistent result was observed in power spectrum as well (see FIG. 3). From the result, it was confirmed that the PLCβ4 knock-out mouse of the present invention had high sensitivity to absence seizure.

In another preferred embodiment of the present invention, the expression of PLCβ4 in a normal mouse was observed by histochemical staining. As a result, PLCβ4 was over-expressed in the thalamic cortex, compared with the expressions in other brain regions. So, the present inventors limited PLCβ4 deficiency specifically in the thalamic cortex and investigated whether or not SWD, one of the characteristics of absence seizure, was observed in the thalamic cortex by PLCβ4 expressed in the thalamic cortex. To construct the thalamic cortex specific PLCβ4 knock-out mouse, shPLCβ4 (Lentivirus containing short hairpin RNA of PLCβ4a) was locally injected into the thalamus relay nuclei of a normal mouse. The expression of PLCβ4 in the thalamic cortex of the PLCβ4 knock-out mouse was observed by histochemical staining. As a result, in the control mouse not injected with shPLCβ4, the expression of PLCβ4 was observed in the thalamic cortex. In the meantime, in the mouse injected with shPLCβ4 containing shRNR of PLCβ4, the expression of PLCβ4 was reduced. That is, it was confirmed that the thalamus specific PLCβ4 expression was efficiently reduced by shPLCβ4 (see FIG. 4).

In a preferred embodiment of the present invention, shPLCβ4 was injected in the thalamus relay nuclei to knock-out PLCβ4 gene locally. Then, EEG was observed in the PLCβ4 knock-out mouse. As a result, spontaneous SWD which was not observed in the control mouse treated with the control vector (pLKO vector) was observed in the PLCβ4 knock-out mouse injected with shPLCβ4. The absence seizure inducing drug RS(+/−)-baclofen was administered into the mouse injected with pLKO vector or shPLCβ4 in its thalamus relay nuclei, followed by observation of brain wave. As a result, SWD was observed longer in the mouse in which local PLCβ4 expression in the thalamic cortex was down-regulated than in the mouse injected with the control vector pLKO. Therefore, it was presumed that PLCβ4 deficiency in the thalamus could be one major reason for absence seizure in the PLCβ4 knock-out mouse (see FIG. 5).

The present inventors also found out that current running through T- and L-type $Ca^{2+}$ channels was increased in thalamocortical neurons of the PLCβ4 knock-out mouse, which resulted in the change of burst firing mode in thalamocortical neurons (Cheong et al, 2008, The Journal of Neuroscience, 28:13331-13340). The present inventors also confirmed that current running through $Ca^{2+}$ channel was reduced by phosphorylation of $Ca^{2+}$ channel when PKC agonist was treated to the PLCβ4 knock-out mouse. Based on the above findings, the present inventors injected the $Ca^{2+}$ channel blockers mibefradil and nifedipine, and the PKC agonists phorbol 12,13-didecanoate (PDD) and phorbol 12-Myristate 13-Acetate (PMA) into the PLCβ4 knock-out mouse limitedly in the region of the thalamus relay nuclei, followed by observation of brain wave. As a result, when the T-, L-, and R-type $Ca^{2+}$ channel blocker mibefradil was treated, hourly SWD was reduced. However, when the L-type $Ca^{2+}$ channel blocker nifedipine was treated, hourly SWD was not changed. In the meantime, when phorbol 12,13-didecanoate and phorbol 12-myristate 13-acetate, the PKC agonists and at the same time known as T-type $Ca^{2+}$ channel blockers, were injected, hourly SWD was reduced (see FIG. 6).

In conclusion, the absence seizure specific SWD is observed in the PLCβ4 knock-out mouse and the SWD is reduced when the absence seizure therapeutic agent is administered, suggesting that the PLCβ4 knock-out mouse can be effectively used as an absence seizure model. When PKC agonist is treated to the PLCβ4 knock-out mouse, the absence seizure animal model of the present invention, absence seizure specific SWD is reduced. Therefore, it is effective for the method for treating absence seizure to include the step of administering a pharmaceutically effective dose of PKC agonist into a subject with absence seizure.

The effective dose of PKC agonist for the treatment is determined by considering administration method, target region, and patient's condition, etc. For the determination of a dose for human, safety and efficiency have to be considered. It is also possible to predict a dose for human from the effective dose determined by animal test.

The composition of the present invention can include generally used carriers, diluents, excipients or mixtures thereof. A pharmaceutically acceptable carrier is any one that can deliver PKC agonist into a target area in vivo. The composition of the present invention can include one or more pharmaceutically acceptable carriers such as saline, sterilized water, Ringer's solution, buffered saline, dextrose solution, maltodextrin solution, glycerol, ethanol, and a mixture comprising one or more of those components. If necessary, general additives such as antioxidants, buffers and bacteriostatic agents can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can be properly formulated according to the disease or components by a proper method known to those in the art.

The composition of the present invention can include one or more effective ingredients having the same or similar function. The composition of the present invention can include the said protein by 0.0001-10 weight %, preferably 0.01-1 weight % by the total weight of the composition.

The composition of the present invention can be administered orally or parenterally (for example, intravenous, hypodermic, local or peritoneal injection). Parenteral administration is preferred, but not always limited thereto. The parenteral administration in this invention is more preferably applied locally to a certain region of the brain, but not always limited thereto.

For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. The composition for the local administration can be formulated as an anhydrous type or a hydrous type according to clinical prescription. Water insoluble excipients and suspensions can contain propylene glycol, polyethylene glycol, vegetable oil like olive oil, injectable ester like ethylolate, etc. Suppositories can contain witepsol, macrogol, tween 61, cacao butter, laurin butter, glycerogelatin, etc.

Solid formulations for oral administration are powders, granules, tablets, soft capsules and pills. Liquid formulation for oral administrations are suspensions, solutions, emulsions, syrups and aerosols, and the abovementioned formulations can contain various excipients such as wetting agents, sweeteners, aromatics and preservatives in addition to generally-used simple diluents such as water and liquid paraffin.

The effective dose of the composition can be determined according to weight, age, gender, health condition, diet, administration time, administration method, excretion and severity of a disease. The dose of the composition of the present invention is 0.0001 mg~10 mg per day and preferably 0.001 mg~2 mg per day, and administration frequency is once a day or preferably a few times a day.

The present invention also provides a method for preventing absence seizure comprising the step of administering a pharmaceutically effective dose of PKC agonist to a subject.

The said PKC agonist is preferably phorbol 12,13-didecanoate (PDD), phorbol 12-Myristate 13-Acetate (PMA), 12-O-tetradecanoyl-phorbol-13-acetate (TPA), bryostatin 1, thrombin, thromboxane mimetic, 1-hexylindolactam-V10, cholesterol sulfate, daphnoretin, decursin, dicaprylglyceride (DiC8), farnesyl thiotriazole, mezerein, 3-ingenyl angelate (PEP005), or sapintoxin A, but not always limited thereto.

In the method of preventing absence seizure of the present invention, the effective dose of PKC agonist is preferably 1~20 pmole, and more preferably 5~15 pmole, but not always limited thereto. The symptoms of absence seizure herein are one or more symptoms selected from the group consisting of seizure, tension-free symptom, fainting and spike-and-wave discharges (SWD), but not always limited thereto. And the SWD is preferably measured by recording EEG. In the method of preventing absence seizure herein, the PKC agonist is preferably administered by parenteral administration pathway, which is preferably intracerebral administration and more preferably intrathalamic administration, but not always limited thereto.

The subject herein is preferably a mammal, which is exemplified by human, non-human primate, mouse, rat, dog, cat, rabbit, horse, and cow, but not always limited thereto.

In a preferred embodiment of the present invention, absence seizure specific SWD was observed in the PLCβ4 knock-out mouse. This kind of brain wave was reduced by ethosuximide that is one of absence seizure therapeutic agents. When γ-butyrolactone and RS(+/−)-baclofen, the absence seizure inducing drugs, were administered, the SWD expression was increased. It was also disclosed in this example by using the mouse model in which PLCβ4 was knocked-out locally in the thalamus relay nuclei that absence seizure specific SWD was related to PLCβ4 gene in the thalamus. To treat absence seizure, the protein kinase C agonist PDD known as a downstream molecule of PLCβ4 was directly injected into the thalamus. As a result, SWD was significantly reduced. So, the present invention confirmed that the PLCβ4 knock-out mouse could be effectively used as an absence seizure animal model and the symptoms of absence seizure observed in the PLCβ4 knock-out mouse could be reduced by the administration of PKC agonist. Therefore, it was also confirmed that the PKC agonist could be effectively used for the prevention of absence seizure.

The present invention provides a composition for the prevention and treatment of absence seizure comprising PKC agonist as an active ingredient.

The said PKC agonist is preferably phorbol 12,13-didecanoate (PDD), phorbol 12-Myristate 13-Acetate (PMA), 12-O-tetradecanoyl-phorbol-13-acetate (TPA), bryostatin 1, thrombin, thromboxane mimetic, 1-hexylindolactam-V10, cholesterol sulfate, daphnoretin, decursin, dicaprylglyceride (DiC8), farnesyl thiotriazole, mezerein, 3-ingenyl angelate (PEP005), or sapintoxin A, but not always limited thereto.

In a preferred embodiment of the present invention, absence seizure specific SWD was observed in the PLCβ4 knock-out mouse. This kind of brain wave was reduced by ethosuximide that is one of absence seizure therapeutic agents. When, the absence seizure inducing drugs, were administered, the SWD pattern in brain wave was increased.

In a preferred embodiment of the present invention, absence seizure specific SWD was reduced by the treatment agent of absence seizure in the PLCβ4 knock-out mouse but was increased, compared with in a normal mouse, by the administration of the absence seizure inducing drugs such as γ-butyrolactone and RS(+/−)-baclofen, suggesting that the PLCβ4 knock-out mouse could be effectively used as an absence seizure animal model. In the meantime, it was proved that the SWD was related to PLCβ4 gene in the thalamus relay nuclei by using the mouse model in which PLCβ4 was knocked-out locally in the thalamus relay nuclei. When PDD, the protein kinase C agonist known as a downstream molecule of PLCβ4, was directly injected into the thalamus, absence seizure specific SWD was reduced. Therefore, the present invention proved that the PLCβ4 knock-out mouse could be effectively used as an absence seizure animal model. It was also confirmed that the PKC agonist could be effectively used for the composition for the prevention and treatment of absence seizure by observing that the symptoms of absence seizure could be alleviated by the administration of PKC agonist in the PLCβ4 knock-out mouse.

The present invention also provides a screening method of PKC agonist for the prevention and treatment of absence seizure comprising the following steps:

1) contacting a sample compound with PKC in vitro;

2) selecting a compound that increased PKC activity, compared with the control untreated with the sample compound of the step 1); and 3) determining whether or not the selected sample compound could be a candidate for the preventive and therapeutic agent for absence seizure.

In a preferred embodiment of the present invention, it was confirmed that the PLCβ4 knock-out mouse could be effectively used as an absence seizure animal model and absence seizure specific SWD was significantly reduced when PKC agonist known as a downstream molecule of PLCβ4 gene was directly injected into the thalamus. The symptoms of absence seizure can be alleviated by the treatment of PKC agonist. So, a sample compound was contacted with PKC in vitro to select a compound that activated PKC. Then, the compound was judged whether it could be a promising candidate for the prevention and treatment of absence seizure. Therefore, the above method could be effectively used for the screening of PKC agonist for the prevention and treatment of absence seizure.

The screening method of PKC agonist candidates is preferably composed of the above steps, but not always limited thereto.

In the screening method of PKC agonist candidates, the PKC activity of step 2) is preferably measured by one of those activities selected from the group consisting of receptor tyrosine kinase (RTK) activity, phosphoinositides-3,4,5-$P_2$ (PtIns-3,4,5-$P_2$) generation, phosphatase and tensin homolog (PTEN) activity inhibition, Akt signal transduction activity and Akt signal downstream signal transduction activity, but not always limited thereto. In the screening method of PKC agonist candidates, the Akt signal transduction activity is preferably measured by one of those activities selected from the group consisting of the activities of BAD, caspase 9, forkhead, inhibitor of kappaB kinase (IKK), endothelial nitric oxide synthase (eNOS), mammalian target of rapamycin (mTOR), and glycogen synthase kinase-3 (GSK3) inhibition, but not always limited thereto.

In the screening method of PKC agonist candidates, it is preferred to decrease the symptoms of absence seizure by treating the selected PKC agonist candidates to the absence seizure animal model, but not always limited thereto.

In the screening method of PKC agonist candidates, the symptoms of absence seizure of step 3) are one or more symptoms selected from the group consisting of seizure, tension-free symptom, fainting and spike-and-wave discharges (SWD), but not always limited thereto.

The present invention also provides a screening method of PKC agonist for the prevention and treatment of absence seizure comprising the following steps:

1) contacting a sample compound with PKC expressing cells in vitro;
2) selecting a compound that increased PKC activity, compared with the control untreated with the sample compound of the step 1); and
3) determining whether or not the selected sample compound could be a candidate for the preventive and therapeutic agent for absence seizure.

In a preferred embodiment of the present invention, it was confirmed that the PLCβ4 knock-out mouse could be effectively used as an absence seizure animal model and absence seizure specific SWD was significantly reduced when PKC agonist known as a downstream molecule of PLCβ4 gene was directly injected into the thalamus. Therefore, the above method could be effectively used for the screening of PKC agonist for the prevention and treatment of absence seizure.

The screening method of PKC agonist candidates is preferably composed of the above steps, but not always limited thereto.

In the screening method of PKC agonist candidates, the PKC activity of step 2) is preferably measured by one of those activities selected from the group consisting of receptor tyrosine kinase (RTK) activity, phosphoinositides-3,4,5-$P_2$ (PtIns-3,4,5-$P_2$) generation, phosphatase and tensin homolog (PTEN) activity inhibition, Akt signal transduction activity and Akt signal downstream signal transduction activity, but not always limited thereto. In the screening method of PKC agonist candidates, the Akt signal transduction activity is preferably measured by one of those activities selected from the group consisting of the activities of BAD, caspase 9, forkhead, inhibitor of kappaB kinase (IKK), endothelial nitric oxide synthase (eNOS), mammalian target of rapamycin (mTOR), and glycogen synthase kinase-3 (GSK3) inhibition, but not always limited thereto.

In the screening method of PKC agonist candidates, it is preferred to decrease the symptoms of absence seizure by treating the selected PKC agonist candidates to the absence seizure animal model, but not always limited thereto.

In the screening method of PKC agonist candidates, the symptoms of absence seizure of step 3) are one or more symptoms selected from the group consisting of seizure, tension-free symptom, fainting and spike-and-wave discharges (SWD), but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Construction of Phospholipaseβ4 Knock-Out Mouse

<1-1> Construction of PLCβ4 Deleted Vector

To separate PLCβ4 gene from mouse genome, the certain region of PLCβ4 cDNA (SEQ. ID. NO: 1) ranging from the starting codon to 226-369$^{th}$ nucleotides was isolated by RT-PCR, which was used as a probe for hybridization to 129/vsJae mouse genome DNA library (LamdaFixll, Stratagene Inc., USA). After selecting genomic clone phage having PLCβ4 gene, it was examined whether or not the gene was PLCβ4 by using restriction enzyme map, Southern blotting and nucleotide sequencing.

To construct PLCβ4 deleted vector, a part of X domain of PLCβ4 protein was eliminated from the PLCβ4 gene clone, which was cloned into PSK-plasmid vector (Stratagene Inc., USA). To increase targeting efficiency, thymidine kinase gene cassette and negative selection marker were inserted into the 3' homologous fragment of the targeting vector containing deleted PLCβ4 gene.

<1-2> Cell Culture

J1 embryonic stem cells were used as a host cell line for the transfection with the above targeting vector constructed in example <1-1>. J1 embryonic stem cells (provided by R. Jeanisch, MIT, USA) were inoculated into ES medium prepared by supplementing 15% fetal bovine serum (Hyclone Co., USA), 1×penicillin-streptomycin, 1× non-essential amino acids (Gibco Co., USA), and 0.1 mM 2-mercaptoethanol to DMEM (Gibco Co., USA), followed by culture at 37° C. for 2-3 days. The embryonic cells prepared from the culture were treated with 1 mM EDTA solution containing 0.25% trypsin to obtain single cells.

<1-3> Introduction of PLCβ4 Deleted Vector Into Cells

Electroporation was performed to transfect the embryonic stem cells separated as single cells in example <1-2> with the targeting vector constructed in example <1-1>. Particularly, the embryonic stem cells diluted at the concentration of 2×10$^7$ cells/ma were mixed with 25 µg of the target vector DNA prepared in example <1-1>, followed by electric shock at 270 V/500 µF. The embryonic stem cells were cultured in ES medium supplemented with 0.3 mg/ml of G418 and 2 µM of ganciclovir for 5-7 days. The embryonic stem cell clone in which PLCβ4 gene was precisely targeted by the targeting vector by homologous recombination was selected by Southern blotting.

<1-4> Generation of PLCβ4+/− Mouse

To generate a chimera mouse having the genotype of PLCβ4+/−, the embryonic stem cell clone selected in example <1-3> was micro-injected into the fertilized blastocyst. Particularly, C57BL/6J female and male mice (Jackson Laboratory, USA) were mated. The 3.5 p.c.(post coitus) female mouse was sacrificed by cervical dislocation. The uterus was extracted from the sacrificed female mouse and the bottom of the uterus was cut by scissors. 1 ml of injection solution comprising 20 mM HEPES, 10% FBS, 0.1 mM 2-mercaptoethanol and DMEM was perfused using a 1 ml syringe. The blastocyst was separated from the uterus tissues by using a micro glass tube under the dissecting microscope. The separated blastocyst was placed in a drop of the injection solution pre-dropped on a 35 mm Petri-dish, which was used for the following experiment.

To introduce the embryonic stem cell clone selected in example <1-3> into the separated blastocyst, 10-15 embryonic stem cell clones were sucked in an injecting pipette, which was inserted into blastocoel of the blastocyst with giving negative pressure to the direction of inner cell mass of the blastocyst by using a holding pipette and then the embryonic stem cell clones were injected into blastocoel of the blastocyst with a microinjector (Zeiss Inc., USA) by changing the pressure to positive. The blastocyst harboring the clones was mated with the vesactomized male mouse, which was transplanted into the uterus of the 2.5 p.c.(post coitus) pseudopregnant surrogate mother mouse to induce a chimera mouse, a kind of cross-bred hybrid, from the embryonic stem cell clone (J1) and the blastocyst of a C57BL/6J mouse. At this time, for the transplantation into the uterus, the abdomen of the surrogate mother anesthetized with avertine (1 mg/kg) was cut 1 cm; the upper part of the uterus was pulled about 2 cm up to the outside of the body with a pincette; a hole was made by an injection needle, and through this hole a micro glass tube was inserted, through which the blastocyst was injected; peritoneal membrane was sewed two stitches with a suture; and the outer skin was sealed with a medical clip. The blastocyst inserted with the embryonic stem cell clone was transplanted into the uterus of the surrogate mother mouse, followed by culture for approximately 19 days, leading to the fusion of embryonic stem cell originated cells and blastocyst originated cells, resulting in the construction of a chimera mouse having the genotype of PLCβ4+/−.

<1-5> Generation of PLCβ4 Knock-Out Mouse

Each chimera mouse was mated respectively with the C57BL/6J and 129sv mice more than 20 times, from which C57BL/6J-PLCβ4+/− and 129sv-PLCβ4+/− mice were generated. The produced mice were mated each other to generate F1 generations 'PLCβ4+/+ and PLCβ4−/−', which were used for the following behavioral tests. The genotype was confirmed by PCR. Primers used for the PCR were K1 (5'-CTC-CACACTCTGCAACCTAC-3'; SEQ. ID. NO. 2), K9 (5'-AGTTACTTCTGGATTTTCAGCC-3'; SEQ. ID. NO. 3) and PFK22 (5'-CTGACTAGGGGAGGAGTAGAAG-3'; SEQ. ID. NO. 4) and PCR was performed as follows: 94° C. for seconds, 58° C. for 30 seconds, and 72° C. for 30 seconds (40 cycles). K1 and K9 primers were the primer set to confirm the genotype of the normal mouse and K1 and PFK22 were the primer set to confirm the genotype of the mutant mouse. Bands corresponding to each PCR product were confirmed on 1.5% EtBr/aragose gel (PLCβ4+/+: 190 bp, PLCβ4+/−: 250/190 by and PLCβ4−/−: 250 bp).

EXAMPLE 2

Mouse Raising and Organization

The mice were raised in SPF (specific pathogen free) environment where temperature was maintained at 22° C. and humidity was regulated at 55% and water and feeds were provided freely under the light cycle of 12 hour light/12 hour dark. The mice for the experiment were all male and 6-18 mice in total. T-test and repeated two-way ANOVA test were performed for the statistical treatment.

EXPERIMENTAL EXAMPLE 1

Spontaneous Absence Seizure in PLCβ4 Knock-Out Mouse

<1-1> SWD Analysis by Measuring EEG

To confirm whether the PLCβ4 in thalamus was related to the generation of absence seizure specific SWD (spike-and-wave discharge), electroencephalogram (EEG) was measured in both the PLCβ4 knock-out mouse and the control normal mouse (PLCβ4(+/+). Epidural electrode was put in the frontal lobe or the parietal lobe, and grounding electrode was put in the occipital region. Tungsten electrode was used to measure the local voltage of the thalamus. EEG was measured with letting the mouse move/behave freely at the 500 Hz sampling speed. Only when the SWD was at least double the base-line voltage and maintained at least 0.5 second in the EEG recording, it was picked up to be analyzed. The electrode locations were confirmed by posthoc histological analysis.

It was confirmed from the result of the analysis of SWD observed during EEG measurement that spontaneous absence seizure accompanying temporary unconsciousness and behavioral arrest was observed when SWD was observed. SWD pattern was dramatically changed in the PLCβ4 knock-out mouse. Spike like slow brain wave was also observed. The average SWD was 87.9±8.8/hour in the PLCβ4 knock-out mouse and the duration of SWD was 1.3±0.1 second at average (FIG. 1B).

<1-2> Measurement of Peak Frequency

To obtain information about elements constituting SWD frequency, power spectrum of spontaneous absence seizure was measured by Fourier analysis. As a result, the peak frequency of SWD was 7.8 Hz in the range of 4-10 Hz (FIG. 1C). Peaks observed at 15.6 Hz and 23.5 Hz were generated by harmonic components of SWD.

<1-3> SWD Reduction by Ethosuximide 200 mg/kg of ethosuximide(ETX) (Sigma, USA), used as a therapeutic agent for absence seizure, was administered to the PLCβ4 PLCbeta4 knock-out mouse and the control normal mouse by intraperitoneal injection. For the control, 0.9% NaCl was administered by intraperitoneal injection. EEG of the mice was recorded for 1 hour. Then, the drug (at the dose of the above) was administered by intraperitoneal injection once. 30 minutes later, EEG was recorded again for 1 hour.

As a result, SWD observed in the PLCβ4 knock-out mouse was significantly reduced in the mouse treated with ethosuximide, compared with the control mouse administered with NaCl (FIG. 1D).

EXPERIMENTAL EXAMPLE 2

Burst Firing Increased in Thalamocortical Neurons of PLCβ4 Knock-Out Mouse

To investigate whether or not burst firing in thalamocortical neurons of the PLCβ4 knock-out mouse affected SWD generation, burst firing in the region of ventrobasal complex(VB) of the brain was observed. Brain sections were prepared from both the PLCβ4 knock-out mouse and the control normal mouse at 4 weeks. Patch clamp experiment was performed according to the method described in the following paper (Cheong E, et al., *Journal of Neuroscience*, 2008). The signal of the brain section was amplified by using Multiclamp 700-A amplifier (Axon Instruments), followed by analysis with pCLAMP 9.2 and Mini-Analysis software (Synaptosoft).

When tonic firing was induced by applying 400 pA of depolarization current, the change of mode from tonic firing into burst firing was easily observed in 15 out of 21 thalamocortical neurons of the PLCβ4 knock-out mouse. This has never happened in all of 17 thalamocortical neurons of the normal mouse (FIGS. 2A and 2B).

Resting membrane potentials of the PLCβ4 knock-out mouse and the normal mouse were respectively −60.24±5.63 mV and −58.74±6.71 mV. Input resistance of each was respectively 167.03±31.45 MΩ and 158.91±29.61 MΩ, suggesting that there was no big difference. Burst firing patterns were observed after applying various hyperpolarization currents. As a result, when the hyperpolarization current ranging from −67~−64 my was applied, a big difference in burst firing was observed. Burst firing was observed in thalamocortical neurons of the PLCβ4 knock-out mouse but not observed at all in thalamocortical neurons of the normal mouse. That is, burst firing that was not observed in the normal control mouse was observed in the PLCβ4 knock-out mouse at the voltage near resting membrane potential (FIGS. 2C, 2D and 2E).

EXPERIMENTAL EXAMPLE 3

Increase of Sensitivity of PLCβ4 Knock-Out Mouse to Absence Seizure by Absence Seizure Inducing Agents γ-butyrolactone (GBL) (Sigma, USA) known as $GABA_BR$ receptor agonist (type B γ-aminobutyric acid receptor agonist) inducing absence seizure and $GABA_B$ receptor specific RS(+/−)-baclofen (Sigma, USA) were administered to the PLCβ4 knock-out mouse and the control normal mouse by intraperitoneal injection. The dose of γ-butyrolactone was 40 mg/kg or 70 mg/kg (intraperitoneal injection). The dose of RS(+/−)-baclofen was 20 mg/kg (intraperitoneal injection).

EEG of those mice was measured before and after the drug administration. As a result, as shown in FIGS. 3B and 3C, spontaneous SWD observed for a short period of time was changed after the intraperitoneal injection (the time point of the administration=0 minute). The change of paroxysmal SWD observed at 2~5 Hz was more significant in the PLCβ4 knock-out mouse than in the control normal mouse. The paroxysmal SWD continued even longer in the PLCβ4 knock-out mouse than in the normal mouse (FIGS. 3B and 3C).

From the power spectrum analysis, it was confirmed that the most powerful spectrum was observed at the frequency range of 2~5 Hz. When the spectrum was in this range, the power increased early and maintained longer (FIGS. 3D and 3E). Therefore, absence seizure was better expressed in the PLCβ4 knock-out mouse when $GABA_B$ receptor agonist was treated.

EXPERIMENTAL EXAMPLE 4

Inhibition of PLCβ4 Expression by shPLCβ4

<4-1> Construction of shPLCβ4 Vector

ShPLCβ4 vector (lentivirus containing shRNA (short hairpin RNA) of PLCβ4) was constructed by the method described in the following paper (Shin J, et al., *Journal of Neuroscience*, 29:15375-15385, 2009), and then tested. As the control vector, pLKO (the vector expressing PLCβ4 non-specific shRNA) was used.

<4-2> Injection of shPLCβ4

The concentrated shPLCβ4 vector and pLKO vector were injected in the thalamus relay nuclei (anteroposterior, −1.82 mm; lateral, ±1.5 mm; ventral −3.5 mm). The mouse was anesthetized with avertine (2,2,2-tribromoethanol). The vectors were injected into the target areas of both hemispheres of the brain using 30 gauge Hamilton syringe by 2 μl at the speed of 0.1 μl/min. 4 weeks after the injection, EEG was measured.

<4-3> Immunostaining Analysis

To perform immunostaining analysis, the brain tissue was frozen, which was cut into coronal sections in 30 μm thickness using microtome according to the procedure described in the following paper (Kang S J, et al, *Molecules and cells*, 25:124-130, 2008). The brain sections were stained with the primary antibody PLCβ4 (Chemicon) and the CY-3 conjugated secondary antibody (Amersham). High definition image of the stained tissue was obtained by using confocal microscopy.

As a result, the PLCβ4 protein was expressed in thalamus relay nuclei (FIG. 4A1) of the control normal mouse, but the expression was very low in cortex (FIG. 4A2).

In the mean time, the PLCβ4 protein expression was not observed in the PLCβ4 knock-out mouse (FIG. 4B).

<4-4> Inhibition of PLCβ4 by shPLCβ4

For the experiment, the highly concentrated shPLCβ4 vector and the control vector pLKO were injected into the thalamocortical relay nuclei of a normal mouse at 8 weeks. To investigate the inhibitory effect of shPLCβ4 on the expression of PLCβ4 protein, immunostaining was performed by the same manner as described in example <4-2>.

As a result, 4 weeks after the injection of the shPLCβ4 vector and the pLKO vector, the normal expression of PLCβ4 was observed in the brain tissue of the mouse injected with the non-specific pLKO vector, while the expression of PLCβ4 was reduced in large area of the thalamocortical relay nuclei of the brain tissue of the mouse injected with the shPLCβ4 vector. Cell number was counted by staining with 4',6-diamidino-2-phenylindole (DAPI) that is the material staining cell nuclei. As a result, it was confirmed that the decrease of cell number which was presumably resulted from the injection of the shPLCβ4 vector and the pLKO vector was not related to the decrease of the PLCβ4 expression (FIGS. 4C and 4D).

EXPERIMENTAL EXAMPLE 5

Induction of Absence Seizure by shPLCβ4

The vectors shPLCβ4 and pLKO were injected into normal mice, and then EEG was measured before and after the injection of RS(+/−)-baclofen. The mutant mice in which thalamic PLCβ4 expression was largely suppressed were selected for the measurement of EEG, considering the region injected with the lentivirus vector and the expression level of PLCβ4 confirmed in experimental example 4.

As a result, spontaneous SWD (7.3±2.0/hour at average) was observed in 7 out of 12 mice. In the meantime, any wave type like spontaneous SWD was not observed in 9 mice treated with the pLKO vector (FIGS. 5A and 5B). Duration of SWD after the injection of RS(+/−)-baclofen in those mice injected with the shPLCβ4 vector was prolonged, compared with in the mice injected with the pLKO vector (FIG. 5C). Therefore, it was confirmed that absence seizure observed in the PLCβ4 knock-out mouse is attributed to the deficiency of PLCβ4 gene in the thalamus.

EXPERIMENTAL EXAMPLE 6

Changes of SWD by PKC Agonist and Calcium Channel Blocker

<6-1> Change of SWD by PKC Agonist

It has been known that PLCβ4-PKC signal transduction in the region of thalamocortex of the PLCβ4 knock-out mouse regulates firing mode of the thalamocortical neurons and pain response can also be regulated thereby (Cheong, E et al., *Journal of Neuroscience*, 2008). After reporting that PKC agonist could regulate firing mode of the thalamocortical neurons, the present inventors wanted to confirm whether or not the spontaneous SWD observed in the thalamocortical neurons of the PLCβ4 knock-out mouse was also mediated by the PLCβ4-PKC signal transduction. To do so, the present inventors measured EEG after injecting the PKC agonist phorbol 12,13-didecanoate (PDD) (Sigma, USA) into the thalamus relay nuclei at the concentration of 10 pmol.

As a result, SWD was not changed in the control group treated with 0.9% NaCl, while SWD was significantly reduced in the group treated with PDD (FIG. 6A).

<6-2> Change of SWD by Calcium Channel Blocker

It was also reported that increased currents of T- and L-type calcium channels of the thalamocortical neurons of the PLCβ4 knock-out mouse and PLCβ4-PKC signal transduction changed firing mode of the thalamocortical neurons (Cheong, E et al., *Journal of Neuroscience*, 2008). Thus, to confirm the cause of the spontaneous SWD observed in the thalamocortical neurons of the PLCβ4 knock-out mouse, PKC agonist and calcium channel blocker were injected locally into the thalamus relay nuclei. Then, SWD generation was observed by measuring EEG.

As a result, SWD was significantly reduced in the group injected with the PKC agonists phorbol 12,13-didecanoate (PDD) (Sigma, USA) and phorbol 12-myristate 13-acetate (PMA) at the concentration of 10 pmol. SWD was significantly reduced in the group treated with the T-type calcium channel blocker mibefradil (Sigma, USA) at the concentration of 1 nmol, but SWD was not changed in the group treated with the L-type calcium channel blocker nifedipine (Sigma, USA) at the concentration of 1 nmol (FIG. 6B). Therefore, it was confirmed that absence seizure observed in the PLCβ4 knock-out mouse was attributed to the inhibition of PKC agonist and the activation of T-type calcium channel.

The Manufacturing Examples of the composition for the present invention are described hereinafter.

MANUFACTURING EXAMPLE 1

Preparation of Pharmaceutical Formulations

| <1-1> Preparation of powders | |
|---|---|
| PKC agonist | 2 g |
| Lactose | 1 g |

Powders were prepared by mixing all the above components, which were filled in airtight packs according to the conventional method for preparing powders.

| <1-2> preparation of tablets | |
|---|---|
| PKC agonist | 100 mg |
| Corn starch | 100 mg |
| Lactose | 100 mg |
| Magnesium stearate | 2 mg |

Tablets were prepared by mixing all the above components by the conventional method for preparing tablets.

| <1-3> Preparation of capsules | |
|---|---|
| PKC agonist | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

| <1-4> Preparation of pills | |
|---|---|
| PKC agonist | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

| <1-5> Preparation of granules | |
|---|---|
| PKC agonist | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

INDUSTRIAL APPLICABILITY

As explained hereinbefore, when PKC agonist was administered into the PLCβ4 knock-out mouse, the absence seizure animal model of the present invention, absence seizure specific SWD was reduced. Therefore, PKC agonist can be effectively used for the composition for the prevention and treatment of absence seizure.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating absence seizure comprising the step of administering a pharmaceutically effective dose of protein kinase C (PKC) agonist selected from the group consisting of phorbol 12, 13-didecanoate (PDD), phorbol 12-myristate 13-acetate (PMA), and mixtures thereof to a subject with absence seizure.

2. The method for treating absence seizure according to claim 1, wherein the pharmaceutically effective dose of PKC agonist is 1~20 pmole.

3. The method for treating absence seizure according to claim 2, wherein the pharmaceutically effective dose of PKC agonist is 10 pmole.

4. The method for treating absence seizure according to claim 1, wherein the subject with absence seizure shows the symptoms selected from the group consisting of seizure, tension-free symptom, fainting and spike-and-wave.

5. The method for treating absence seizure according to claim 1, wherein the subject is treated by parenteral administration of the PKC agonist.

6. The method for treating absence seizure according to claim 5, wherein the parenteral administration is intracerebral administration.

7. The method for treating absence seizure according to claim 6, wherein the intracerebral administration is intrathalamic administration.

* * * * *

SEQUENCE LISTING

<160> NUMBER OF SEQ ID NOS: 4

<210> SEQ ID NO 1
<211> LENGTH: 3528
<212> TYPE: DNA
<213> ORGANISM: Mus musculus

```
<400> SEQUENCE: 1
atggccaaac cttacgaatt taactggcag aaggaagtgc cctctttctt gcaagaagga     60 gcagttttg acagatacga agaggaatct tttgtgtttg agcccaactg cctcttcaaa    120
gtagatgaat tcggcttctt cctgacgtgg aagagtgaag gcaaggaagg acaagtgcta    180
gaatgttccc tcatcaacag tattcgccaa gcagccatac caaaggatcc caaaatcctg    240
gctgctctcg aagctgttgg aaaatctgaa aatgatctgg aagggcggat attgtgtgtc    300
tgcagcggca cggatctggt gaatatcggc ttcacttaca tggtggctga aaatccagaa    360
gtaactaagc aatgggtaga aggcctgaga tcgatcattc acaacttcag ggcaaacaac    420
gtcagtccga tgacatgcct caagaaacac tggatgaaac tggccttctc gaccaacaca    480
actggtaaaa tcccagtgag gagtatcact agaaccttcg catcagggaa aacagaaaag    540
gtgatctttc aagccctcaa ggaactaggt cttcccagtg aaagaatgat gaaattgaa    600 cctgctgcat ttacttatga aaagttctat gaactgacac aaaagatttg tcctcggaca    660
gatatagaag atcttttaa aaaaatcaat ggagacaaaa ctgattattt aacggtagac    720
caattagtga gctttctaaa cgaacatcag cgagatcctc ggctgaatga atttttattc    780
ccattttatg atgctaaaag agcaatgcag atcattgaaa tgtatgagcc tgatgaagag    840
ctgaagaaaa aaggcctcat atccagtgat ggattctgca gatatctgat gtcagatgaa    900
aatgcccctg tcttcttaga tcgcttagaa ctttaccagg agatggacca cccgctggct    960
cattacttca tcagttcctc ccacaacacc tatctcactg gccggcaatt tggaggaaag   1020
tcttcagtgg aaatgtacag acaagttctc ctggctggtt gcaggtgtgt tgaacttgac   1080
tgttgggatg gaaaaggtga agatcaggaa ccgataataa ctcacggaaa agcaatgtgt   1140
acagacatcc ttttaagga tgtaatccag gccatcaagg aaacggcgtt tgtcacatca   1200 gaatacctg tcattctctc cttcgaaaac cactgcagca aatatcaaca gtacaagatg   1260
tccaagtatt gtgaagatct atttggggat ctcctgttga acaagcact tgagtcgcat   1320 ccacttgaac caggaaggcc cttgccgtct cctaatgacc tcaaaagaaa aatactcatc   1380
aagaataaga ggctgaagcc tgaagttgaa aagaaacagc ttgaagcttt gaaaagcatg   1440
atggaagctg agagtcagc cgccccagct agcatcttgg aagacgacaa tgaagaggaa   1500
atagaaagtg ctgatcaaga ggaagaagcc caccctgaat acaaatttgg aaatgaactt   1560
tctgccgatg actacagtca aaggaagcg gttgcaaaca gcgtcaagaa gggcctggtc   1620
accgtagagg atgagcaagc atggatggca tcttataaat acgtaggtgc taccacgaac   1680
atccatccgt acttgtccac gatgatcaac tatgcccagc cgtgaagtt tcaaggtttc   1740 cacgtggctg aagagcgcaa tattcactat aacatgtctt cttttaacga gtcggttggc   1800
cttggctact tgaagacgca cgcgattgag tttgtaaatt acaataagcg acaaatgagc   1860
cgcatttacc ccaagggagg ccgagttgat tccagtaatt acatgcctca gattttctgg   1920
aacgctggtt gccagatggt ttcactgaac tatcaaaccc cagatttagc gatgcaattg   1980
aatcaaggaa aatttgagta taatggatca tgcgggtacc ttctcaagcc agatttcatg   2040
aggcggcctg atcggacatt tgaccccttc tctgaaaccc ctgtggacgg ggttattgca   2100
gccacgtgct cagtgcaggt tatatcaggg cagttcctct cagataagaa gatcgggaca   2160
tacgtggaag tcgatatgta cgggctgccc accgacacca tacggaaaga gttccgaacc   2220
cgcatggtta tgaacaatgg actcaaccca gtgtataatg aagaatcgtt tgtgttcgga   2280
aaggtgatcc tgcctgacct agctgtcctg agaatcgcag tctacgatga caacaacaag   2340
```

-continued

```
ctaattggcc agaggatcct tcctttggat ggtctccaag caggctaccg acacatctcc    2400
ctgagaaacg agggaaacaa accattatca ctgccaacaa ttttctgcaa tattgttctt    2460
aaaacatacg tgcctgatgg atttggagat attgtggatg ctttatccga tccaaagaaa    2520
tttctttcaa tcacagagaa gagagcagac caaatgagag caatgggcat tgaaactagt    2580
gacatagcag atgtgcccag tgacacttcc aaaaatgaca agaaaggcaa ggccaaccca    2640
gccaaagcga acgtgacccc tcagagcagc tctgagctca gaccaaccac cacagccgcc    2700
ctgggctctg gccaggaagc caagaaaggt attgaactta ccctcaagt gaggatagaa     2760 gatttaaagc aaatgaaggc ttacttgaag catttaaaga acaacagaa ggagttaaac     2820 tctttaaaga agaaacatgc aaaggagcac agtaccatgc agaagttaca ctgcacacaa    2880
gttgacaaaa tcgtggccca gtatgacaaa gagaagtcga ctcatgagaa aatcctagag    2940
aaggcgatga agaagaaggg gggaagtaat tgtcttgaaa taaaaaaaga aacagaaatt    3000
aaaattcaga ccctgacaac ggatcacaaa tctaaggtca aagagattgt ggcccagcac    3060
acaaaggagt ggtcagaaat gatcaacact cacagtgcgg aggagcagga atccgggat    3120 ctgcacctga gccagcagtg tgagctgctg agaaagctgc tcatcaatgc tcatgagcag    3180
cagacccagc agctgaaact ccccatgac agggaaagca aggagatgag agcccatcag    3240
gctaagattt ctatggaaaa tagcaaggcc atcagtcaag ataaatctat caagaacaag    3300
gcagaacggg aaaggcgagt cagggagttg aacagcagca acactaagaa gttcctagaa    3360
gaaagaaaga gactggcgat gaagcagtca aagaaatgg atcagttgaa aaaagtccag    3420
ctggagcacc tagaattcct agagaaacag aacgagcagg cgaaggagat gcagcagatg    3480
gtgaaattgg aagccgagat ggaccgcaga ccagcaacag tagtatga                 3528
```

```
<210> SEQ ID NO 2
<211> LENGTH: 20
<212> TYPE: DNA
<213> ORGANISM: Artificial Sequence
<220> FEATURE:
<223> OTHER INFORMATION: K1 primer

<400> SEQUENCE: 2
ctccacactc tgcaacctac                                                  20

<210> SEQ ID NO 3
<211> LENGTH: 22
<212> TYPE: DNA
<213> ORGANISM: Artificial Sequence
<220> FEATURE:
<223> OTHER INFORMATION: K9 primer

<400> SEQUENCE: 3
agttacttct ggattttcag cc                                               22

<210> SEQ ID NO 4
<211> LENGTH: 22
<212> TYPE: DNA
<213> ORGANISM: Artificial Sequence
<220> FEATURE:
<223> OTHER INFORMATION: PGK22 primer

<400> SEQUENCE: 4
ctgactaggg gaggagtaga ag                                               22
```